United States Patent [19]

Alig et al.

[11] 4,131,655
[45] Dec. 26, 1978

[54] D-HOMOPREGNANES

[75] Inventors: Leo Alig, Kaiseraugst; Andor Fürst, Basel; Marcel Müller, Frenkendorf, all of Switzerland; Ulrich Kerb; Rudolf Wiechert, both of Berlin, Germany

[73] Assignee: Hoffman-La Roche Inc., Nutley, N.J.

[21] Appl. No.: 898,070

[22] Filed: Apr. 20, 1978

[30] Foreign Application Priority Data

Apr. 21, 1977 [LU] Luxembourg ............................ 77173
Jan. 6, 1978 [CH] Switzerland ........................... 139/78

[51] Int. Cl.² .................... C07F 9/09; C07C 49/44
[52] U.S. Cl. ................................ 260/946; 560/61;
560/62; 560/64; 560/65; 560/43; 560/107;
560/194; 560/257; 260/457; 260/586 E;
424/214; 424/266; 424/303; 424/308; 424/309;
424/310; 424/313; 424/331; 546/263; 546/285
[58] Field of Search ............... 260/294.8 A, 295.5 P,
260/457, 946, 586 E; 560/61, 62, 64, 65, 43,
107, 194, 257

[56] References Cited

U.S. PATENT DOCUMENTS

| | | | |
|---|---|---|---|
| 3,939,193 | 2/1976 | Alig et al. ........................ | 260/586 E |
| 4,036,874 | 7/1977 | Alig et al. ........................ | 260/586 E |
| 4,057,561 | 11/1977 | Fürst et al. ...................... | 260/586 E |

FOREIGN PATENT DOCUMENTS

| | | | |
|---|---|---|---|
| 803462 | 2/1974 | Belgium ............................ | 260/586 E |
| 2448662 | 4/1976 | Fed. Rep. of Germany ....... | 260/586 E |

OTHER PUBLICATIONS

Heller et al., Steroids 7, 381 (1966).

Primary Examiner—Gerald A. Schwartz
Attorney, Agent, or Firm—Samuel L. Welt; George M. Gould; Raymond R. Wittekind

[57] ABSTRACT

D-homopregnanes of the formula

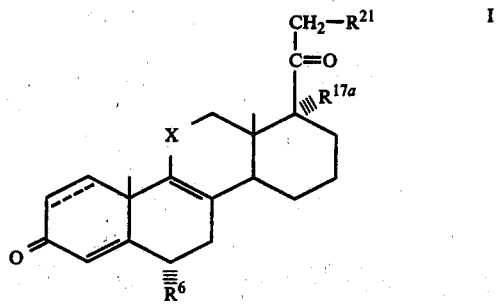

wherein $R^6$ is hydrogen, chloro, fluoro or methyl; X is β-hydroxymethylene or carbonyl; $R^{17a}$ is hydroxy, lower alkanoyloxy or aroyloxy; $R^{21}$ is hydrogen, chloro, fluoro, hydroxy, lower alkanoyloxy, aroyloxy, sulfate or phosphate; and the dotted line in the 1,2-position of the A-ring denotes an additional carbon-carbon bond and pharmaceutically acceptable salts thereof, processes for the preparation thereof and pharmaceutical compositions containing them as the active ingredient are disclosed. The D-homopregnanes of the present invention exhibit hormonal activity and are useful for the treatment of inflammation.

20 Claims, No Drawings

D-HOMOPREGNANES

DESCRIPTION OF THE INVENTION

The present invention relates to novel D-homosteroids. More particularly, the invention is concerned with D-homopregnanes, processes for the preparation thereof and pharmaceutical compositions containing them as the active ingredient.

The D-homosteroids provided by the present invention are compounds of the formula

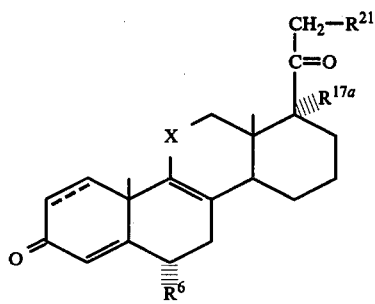

I wherein $R^6$ is hydrogen, chloro, fluoro or methyl; X is β-hydroxymethylene or carbonyl; $R^{17a}$ is hydroxy, lower alkanoyloxy or aroyloxy; $R^{21}$ is hydrogen, chloro, fluoro, hydroxy, lower alkanoyloxy, aroyloxy, sulfate or phosphate; and the dotted line in the 1,2-position of the A-ring denotes an additional carbon-carbon bond and pharmaceutically acceptable salts thereof.

As used throughout the specification and appended claims, the term "alkanoyloxy" denotes the residue obtained by removal of the hydroxy proton of the carboxylic acid group of straight- or branched-chain, saturated or unsaturated aliphatic mono- or dicarboxylic acids which may be substituted by hydroxy or amino groups or by halogen atoms. Examples of the aforementioned alkanoyloxy groups which contain preferably from 1 to 15 carbon atoms are formyloxy, acetoxy, propionyloxy, butyryloxy, pentanoyloxy, hexanoyloxy, octanoyloxy, undecanoyloxy, dimethylacetoxy, trimethylacetoxy, diethylacetoxy, tert. butylacetoxy, phenacetoxy, cyclopentylpropionyloxy, hydroxyacetoxy, mono-chloroacetoxy, dichloroacetoxy, trichloroacetoxy, dimethylaminoacetoxy, succinoyloxy and ω-carboxypentanoyloxy groups. The term "aroyloxy" denotes the residue obtained by removal of the hydroxy proton of the carboxylic acid group of aromatic carboxylic acid which may be substituted by hydroxy or amino groups or by halogen atoms. Examples of the aforementioned aroyloxy groups are benzoyloxy and nicotinoyloxy. Analogously, the terms "alkanoyl" and "aroyl" denote the residue obtained by removal of the hydroxy group of the carboxylic acid function from straight- or branched-chain, saturated or unsaturated aliphatic mono- or dicarboxylic acids and aromatic carboxylic acids, respectively, the compounds of both series of which may be substituted by hydroxy or amino groups or by halogen atoms. Formyl, acetyl, propionyl, etc., and benzoyl and nicotinoyl are examples of the aforementioned alkanoyl and aroyl groups, respectively. The term "lower" denotes a group having a carbon skeleton containing 1 to 8 carbon atoms.

In order to obtain water-soluble substances, the 21-alkanoyloxy or 21-aroyloxy compounds containing a basic nitrogen atom in the alkanoyloxy or aroyloxy group may be converted into the corresponding acid addition salts such as, for example, hydrochlorides, hydrobromides, sulfates, phosphates, tartrates or maleates and the monoesters of polycarboxylic acids as well as the sulfuric and phosphoric acid esters may be converted into their alkali salts, for example, sodium or potassium salts or into ammonium salts.

In the formulas presented herein, the various substituents are joined to the cyclic nucleus by one of three notions: a solid line (—), indicating a substituent which is in the β-orientation (above the plane of the paper), a dotted line (╌), indicating a substituent which is in the α-orientation (below the plane of the paper), or a wavy line (∿), indicating a substituent which may either be in the α- or β-orientation. The position of the methyl groups in the 10- and 13-positions have been arbitrarily indicated as the β-orientation which is consistent with the absolute stereochemistry of the products described in the examples. It is to be understood, however, that in the formulas presented both in the specification and in the appended claims, there is intended to be represented both of the enantiomeric series, as well as mixtures thereof, such as racemic mixtures.

Preferred D-homosteroids provided by the present invention are compounds of formula I wherein X is hydroxymethylene and $R^{21}$ is hydrogen, hydroxy, alkanoyloxy or phosphate and salts thereof. Also preferred are D-homosteroids of formula I wherein $R^6$ is methyl or fluoro.

Examples of compounds of formula I are:
21-acetoxy-11β,17a-dihydroxy-D-homopregna-1,4,8-triene-3,20-dione;
11β,17a-dihydroxy-D-homopregna-1,4,8-triene-3,20-dione;
17a-butyryloxy-11β-hydroxy-D-homopregna-1,4,8-triene-3,20-dione;
17a,21-bis(butyryloxy)-11β-hydroxy-D-homopregna-1,4,8-triene-3,20-dione;
17a,21-bis(butyryloxy)-6α-fluoro-11β-hydroxy-D-homopregna-1,4,8-triene-3,20-dione;
21-acetoxy-6α-fluoro-11β,17a-dihydroxy-D-homopregna-1,4,8-triene-3,20-dione;
21-acetoxy-17a-hydroxy-D-homopregna-1,4,8-triene-3,11,20-trione;
11β,17a,21-trihydroxy-D-homopregna-1,4,8-triene-3,20-dione;
6α-fluoro-11β,17a,21-trihydroxy-D-homopregna-1,4,8-triene-3,20-dione;
21-acetoxy-11β,17a-dihydroxy-6α-methyl-D-homopregna-1,4,8-triene-3,20-dione;
11β,17a,21-trihydroxy-6α-methyl-D-homopregna-1,4,8-triene-3,20-dione;
Δ⁸-D-homoprednisone-21-phosphate;
17a,21-dihydroxy-D-homopregna-1,4,8-triene-3,11,20-trione;
Δ⁸-D-homoprednisolone-21-hemisuccinate;
Δ⁸-6α-fluoro-D-homoprednisolone-21-hemisuccinate; and
Δ⁸-6α-methyl-D-homoprednisolone-21-hemisuccinate.

The D-homosteroids of formula I and the salts thereof are prepared in accordance with the present invention by cleaving hydrogen bromide from a compound of the formula

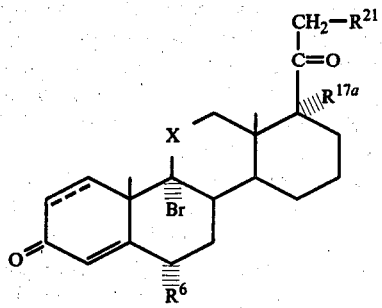

wherein $R^6, X, R^{17a}, R^{21}$ and the dotted line in the 1,2-position of the A-ring are as above and, if desired, saponifying the alkanoyloxy or aroyloxy group, esterifying the hydroxy group present in the 17a- and/or 21-position, oxidizing the 11-hydroxy group, dehydrogenating the 1,2-position of the A-ring and/or converting the compound of formula I so obtained into a salt.

The cleavage of hydrogen bromide from a compound of formula II can be carried out under conditions which are conventionally used in steroid chemistry for the cleavage of hydrogen bromide from bromohydrins or α-bromoketones. Thus, for example, the cleavage of hydrogen bromide can be carried out by heating a compound of formula II in a tertiary amine such as pyridine, lutidine or, particularly, collidine, preferably under reflux. An additional method for the cleavage of hydrogen bromide comprises, for example, reacting a compound of formula II with lithium salts and/or calcium carbonate in dimethylformamide or dimethylacetamide.

The oxidation of an 11β-hydroxy-D-homosteroid of formula I to the corresponding 11-oxo-D-homosteroid of formula I is carried out according to methods known in the art, for example, by chromic acid, N-bromosuccinimide or N-bromoacetamide.

The saponification of a 17a- and/or 21-alkanoyloxy or -aroyloxy group is carried out according to methods known in the art. For example, the saponification can be carried out in water or aqueous alcohols in the presence of acid catalysts such as, for example, hydrochloric acid, sulfuric acid or p-toluenesulfonic acid, or of basic catalysts such as, for example, potassium hydrogen carbonate, potassium carbonate, sodium hydroxide or potassium hydroxide.

The esterification of free hydroxy groups present in the 17a- and/or 21-position is likewise carried out according to methods known in the art. Thus, for example, the esterification can be carried out with alkanoyl or aroyl chlorides or anhydrides in the presence of acids such as, for example, hydrochloric acid, p-toluenesulfonic acid or trifluoroacetic acid, or in the presence of bases such as, for example, potassium carbonate, pyridine, collidine or p-dimethylaminopyridine. The esterification can also be carried out with carboxylic acids in the presence of trifluoroacetic acid anhydride.

The 21-monosulfuric acid esters can be prepared from 21-hydroxy compounds of formula I by methods known in the art, for example, by reaction with sulfur trioxide in pyridine. If desired, the resulting sulfuric acid esters can be converted into alkali salts by treatment with alkali bases.

The phosphoric acid esters can be prepared from 21-hydroxy compounds of formula I by methods known in the art, for example, by reaction with phosphorus halides, preferably pyrophosphoryl chloride, followed by hydrolysis. If desired, the resulting phosphoric acid esters can be converted into alkali metal salts by treatement with alkalis.

The 1,2-dehydrogenation of a compound of formula I in which a single bond is present in the 1,2-position can be carried out by methods known in the art, for example, microbiologically or by means of dehydrogenating agents such as iodine pentoxide, periodic acid, selenium dioxide, 2,3-dichloro-5,6-dicyanobenzoquinone, chloranil or lead tetraacetate. Suitable microorganisms which can be used for the 1,2-dehydrogenation are Schizomycetes, especially those of the genera Arthrobacter, for example, A. simplex, Bacillus, for example, B. lentus and B. sphaericus, Pseudomonas, for example, P. aeruginosa, Flavobacterium, for example, F. flavenscens, Lactobacillus, for example, L. brevis and Nocardia, for example, N. opaca.

The starting materials of formula II are either known or can be prepared by methods analogous to those used for the preparation of described compounds.

The D-homosteroids provided by the present invention possess hormonal activity. In particular, they possess a pronounced antiinflammatory activity when administered topically. The following Table shows the results obtained with two compounds of formula I in standard tests which illustrate the activity of this class of compounds. The tests are carried out as follows:

1. Vasoconstriction test

This test demonstrates the antiinflammatory activity on experimentally hyperemiated skin. See Brit. J. Derm. 69, 11 (1957). In this test, the degree of vasoconstriction in relation to the time was estimated visually (after 4 and 8 hours). The color value of the hyperemiated non-treated skin was rated as 0 and the color value of the non-hyperemiated skin was rated as 100. The compounds were used in a concentration of 0.001% and 0.00001%.

2. Felt pellet test

Two felt pellets were implanted under the skin (scapula region) in female rats (90–110 g.) under ether narcosis. The compounds to be tested were administered orally on four successive days commencing on the day of the implantation. On the fifth day the rats were sacrificed and the granulomas formed were removed, dried and weighed. The $ED_{40}$, namely that dosage which gave a 40% reduction of the granulation weight, was determined.

Table

| Compound | Test Vasoconstriction 4 hours/8 hours concentration | | Felt pellet $ED_{40}$ (mg/kg) |
|---|---|---|---|
| | 0.001% | 0.00001% | |
| 6α-Fluoro-11β, 17a, 21-trihydroxy-D-homopregna-1,4,8-triene-3,20-dione | 71/77 | 55/61 | 0.2 |
| 11β, 17a,21-Trihydroxy-D-homopregna-1,4,8-triene-3,20-dione | 62/69 | 25/33 | 2.6 |

The D-homosteroids provided by the present invention can be used for the treatment of inflammatory conditions.

The D-homosteroids provided by the present invention can be used as medicaments; for example, in the form of pharmaceutical preparations having direct or delayed liberation of the active ingredient which contain them in association with a compatible pharmaceutical carrier material. This carrier material can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly, etc. The pharmaceutical preparations ca be made up in a solid form, for example, as tablets, dragees, suppositories or capsules, in a semi-solid form, for example, as salves, or in a liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers.

In general, the dosage range in the case of pharmaceutical preparations for topical administration can be about 0.00001–5% of a compound of formula I. In the case of pharmaceutical preparations for enteral or parenteral administration about 0.05–50 mg. of active ingredient can be used per administration.

The pharmaceutical preparations can be prepared by methods known in the art by mixing a D-homosteroid of formula I with non-toxic solid and/or liquid carrier materials which are customary inn pharmaceutical preparations and which are suitable for therapeutic administration, for example, those carrier materials mentioned earlier and, if desired, transforming the mixture into the desired pharmaceutical dosage form.

The following Examples illustrate the process provided by the present invention.

EXAMPLE I 2 g. of 21-acetoxy-9-bromo-11$\beta$, 17a-dihydroxy-D-homopregna-1,4-diene-3,20-dione were boiled at reflux in 10 ml. of collidine for 35 minutes under argon. The mixture was cooled and diluted with methylene chloride. The methylene chloride solution was washed with ice-cold hydrochloric acid, sodium hydrogen carbonate solution and sodium chloride solution, dried over sodium sulfate and evaporated. Chromatography of the residue on silica gel gave 21-acetoxy-11$\beta$, 17a-dihydroxy-D-homopregna-1,4,8-triene-3,20-dione of melting point 229–231° C.; $[\alpha]_D = +9°$ (c = 0.1% in methanol); UV: $\epsilon_{241} = 14920$.

By the method of Example 1,
from 9-bromo-11$\beta$,17a-dihydroxy-D-homopregna-1,4-diene-3,20-dione there was obtained 11$\beta$,17a-dihydroxy-D-homopregna-1,4,8-triene-3,20-dione of melting point 183–184° C.; $[\alpha_3 = -68°$ (c = 0.1% in dioxane); UV: $\epsilon_{240} = 14950$;

from 9-bromo-17a-butyryloxy-11$\beta$-hydroxy-D-homopregna-1,4-diene-3,20-dione there was obtained 17a-butyryloxy-11$\beta$-hydroxy-D-homopregna-1,4,8-triene-3,20-dione of melting point 226° C.; $[\alpha]_D = -96°$ (c = 0.1% in dioxane); UV: $\epsilon_{242} = 15400$;

from 9-bromo-17a,21-bis(butyryloxy)-11$\beta$-hydroxy-D-homopregna-1,4:diene-3,20-dione there was obtained 17a, 21-bis(butyryloxy)-11$\beta$-hydroxy-D-homopregna-1,4,8-triene-3,20-dione of melting point 202–203° C.; $[\alpha]_D = -49°$ (c = 0.1% in dioxane); UV: $\epsilon_{241} = 15700$;

from 9-bromo-17a,21-bis(butyryloxy)-6$\alpha$-fluoro-11$\beta$-hydroxy-D-homopregna-1,4-diene-3,20-dione there was obtained 17a,21-bis(butyryloxy)-6$\alpha$-fluoro-11$\beta$-hydroxy-D-homopregna-1,4,8-triene-3,20-dione of melting point 190–191° C.; $[\alpha]_D = -30°$ (c = 0.1% in dioxane); UV: $\epsilon_{241} = 16600$;

from 21-acetoxy-9-bromo-6$\alpha$-fluoro-11$\beta$, 17a-dihydroxy-D-homopregna-1,4-diene-3,20-dione there was obtained 21-acetoxy-6$\alpha$-fluoro-11$\beta$, 17a-dihydroxy-D-homopregna-1,4,8-triene-3,20-dione of melting point 212°–213° C.; $[\alpha]_D = +29°$ (c = 0.1% in dioxane); UV: $\epsilon_{239} = 16070$;

from 21-acetoxy-9-bromo-11$\beta$,17a-dihydroxy-6$\alpha$-methyl-D-homopregna-1,4-diene-3,20-dione there was obtained 21-acetoxy-11$\beta$, 17a-dihydroxy-6$\alpha$-methyl-D-homopregna-1,4,8-triene-3,20-dione of melting point 238°–239° C.; UV: $\epsilon_{241} = 15600$;

from 21-acetoxy-9-bromo-11$\beta$,17a-dihydroxy-D-homopregn-4-ene-3,20-dione there was obtained 21-acetoxy-11$\beta$,17a-dihydroxy-D-homopregna-4,8(9)-diene-3,20-dione of melting point 178°–188° C. (decomposition); $[\alpha]_D = +167°$ (c = 0.1% in dioxane); UV: $\epsilon_{239} = 15860$; and from 9-bromo-17a-butyryloxy-21-chloro-11$\beta$-hydroxy-D-homopregna-1,4-diene-3,20-dione there was obtained 17a-butyryloxy-21-chloro-11$\beta$-hydroxy-D-homopregna-1,4,8-triene-3,20-dione of melting point 183.5°–184° C.; $[\alpha]_D = -62°$ (c = 0.1% in dioxane); UV: $\epsilon_{242} = 15500$.

EXAMPLE 2

104 mg. of 21-acetoxy-11$\beta$,17a-dihydroxy-D-homopregna-1,4,8-triene-3,20-dione in 10 ml. of acetone were treated with 0.09 ml. of Jones reagent and stirred at 25° C. After 15 minutes, the mixture was diluted with methylene chloride, washed with water and dilute sodium chloride solution, dried and evaporated. Crystallization of the residue from acetone/hexane yielded 21-acetoxy-17a-hydroxy-D-homopregna-1,4,8-triene-3,11,20-trione of melting point 211°–215° C.; $[\alpha]_D = +356°$ (c = 0.1% in dioxane); UV: $\epsilon_{241} = 20500$.

EXAMPLE 3

200 mg. of 21-acetoxy-11$\beta$,17a-dihydroxy-D-homopregna-1,4,8-triene-3,20-dione in 10 ml. of methanol were treated with 80 mg. of potassium carbonate in 1 ml. of water and the mixture was stirred under argon for 40 minutes. 0.1 ml. of acetic acid was then added and the methanol was evaporated off in vacuo. The residue was purified by shaking-out in methylene chloride and water. After drying and evaporating the methylene chloride soluiton and crystallization of the residue from acetone/hexane, there was obtained 11$\beta$,17a,21-trihydroxy-D-homopregna-1,4,8-triene-3,20-dione of melting point 210°–213° C.; $[\alpha]_D = -29°$ (c = 0.1% in dioxane); UV: $\epsilon_{240} = 12400$.

By the method of Example 3,
from 21-acetoxy-6$\alpha$-fluoro-11$\beta$,17a-dihydroxy-D-homopregna-1,4,8-triene-3,20-dione there was obtained 6$\alpha$-fluoro-11$\beta$,17a,21-trihydroxy-D-homopregna-1,4,8-triene-3,20-dione of melting point 157°–159° C.; $[\alpha]_D = +5°$ (c = 0.1% in dioxane); UV: $\epsilon_{240} = 15920$;

from 21-acetoxy-17a-hydroxy-D-homopregna-1,4,8-triene-3,11,20-trione there was obtained 17a,21-dihydroxy-D-homopregna-1,4,8-triene-3,11,20-trione of melting point 207°–209° C.; $[\alpha]_D = +341°$ (c = 0.1% in dioxane); UV: $\epsilon_{241} = 19700$; and from 21-acetoxy-11$\beta$,17a-dihydroxy-6$\alpha$:methyl-D-homppregna-1,4,8-triene-3,20-dione there was obtained 11$\beta$,17a,21-:trihydroxy-6$\alpha$-methyl-D-homopregna-1,4,8-triene-3,20-dione of melting point 199-200° C.; $[\alpha]_{365} = +60°$ (c = 0.1% in dioxane); UV: $\epsilon_{241} = 15000$.

EXAMPLE 4

375 mg. of 11β,17a,21-trihydroxy-D-homopregna-1,4,8-triene-3,20-dione and 0.5 ml. of acetic acid anhydride in 5 ml. of pyridine were stirred at 0° C. After 5 hours, 1 ml. of methanol was added and the mixture was stirred at room temperature for a further 15 minutes. The mixture was then diluted with methylene chloride and the solution was washed with ice-cold 2N hydrochloric acid, water and dilute sodium chloride solution, dried over sodium sulfate and evaporated. Crystallization of the residue gave 21-acetoxy-11β,17a-dihydroxy-D-homopregna-1,4,8-triene-3,20-dione of melting point 229°–231° C.; $[\alpha]_D = +9°$ (c = 0.1% in methanol); UV: $\epsilon_{241} = 14920$.

EXAMPLE 5

100 mg. of 17a,21-dihydroxy-D-homopregna-1,4,8:triene-3,11,20-trione in 5 ml. of tetrahydrofuran were treated at −30° C. with 0.1 ml. of pyrophosphoryl chloride and the mixture was stirred at −30° C. for 1.5 hours. 5 ml. of water were added cautiously and the mixture was then heated on a steam-bath for 5 minutes. The mixture was then poured into ca 100 ml. of ethyl acetate and washed three times with ca 10 ml. of water. Evaporation of the ethyl acetate solution yielded $\Delta^8$-D-homoprednisone-21-phosphate in the form of an amorphous powder of melting point 159°–165° C. (from ethyl acetate/ether); $[\alpha]_D = +251°$ (c = 0.1% in methanol); UV: $\epsilon_{242}$ " 18000.

The following examples illustrte typical pharmaceutical preparations containing a D-homosteroid of formula I of the present invention as the active ingredient.

Example A

| Active ingredient | 0.01 wt. % |
|---|---|
| Liquid paraffin | 10.0 wt. % |
| White soft paraffin q.s. ad | 100 parts by weight |

The active ingredient, the D-homosteroid of formula I, is ground with a portion of the liquid paraffin in a ball mill until a particle size of less than 5 μ is attained. The paste is diluted and the ball mill is washed out with the remainder of the liquid paraffin. The suspension is added to the melted colorless while paraffin at 50° C. and the mixture is stirred until it becomes cold, there being obtained a homogeneous salve.

Example B

| Active ingredient | 0.25 wt. % |
|---|---|
| Aluminum stearate | 3.2 wt. % |
| Liquid paraffin q.s. ad | 100 parts by weight |

The aluminum stearate is dispersed in the liquid paraffin by vortex-stirring. The suspension is heated with further stirring, the temperature increase being carried out at a rate of 2° C. per minute until a temperature of 90° C. is attained. The temperature is held at 90° C. to 95° C. for 30 minutes until a gel is formed. It is then cooled rapidly. The active ingredient, the D-homosteroid of formula I, is milled to a particle size of below 5 μ, ground thoroughly with a small portion of the gel and finally worked into the remainder of the gel, there being thus obtained a homogeneous mixture.

We claim:
1. A compound of the formula

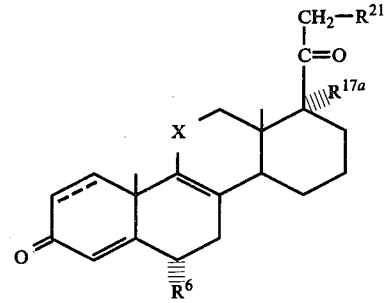

wherein $R^6$ is hydrogen, chloro, fluoro or methyl; X is β-hydroxymethylene or carbonyl; $R^{17a}$ is hydroxy, lower alkanoyloxy or aroyloxy; $R^{21}$ is hydrogen, chloro, fluoro, hydroxy, lower alkanoyloxy, aroyloxy, sulfate or phosphate; and the dotted line in the 1,2-position of the A-ring denotes an additional carbon-carbon bond
or a pharmaceutically acceptable salt thereof.

2. The compound according to claim 1 wherein $R^6$ is hydrogen, fluoro or methyl; X is hydroxymethylene; and $R^{21}$ is hydrogen, hydroxy, lower alkanoyloxy or phosphate.

3. The compound according to claim 2 which is 21-acetoxy-11β,17a-dihydroxy-D-homopregna-1,4,8-triene-3,20-dione.

4. The compound according to claim 2 which is 11β,17a-dihydroxy-D-homopregna-1,4,8-triene-3,20-dione.

5. The compound according to claim 2 which is 21-acetoxy-11β,17a-dihydroxy-6α-methyl-D-homopregna-1,4,8-triene-3,20-dione.

6. The compound according to claim 2 which is 17a-butyryloxy-11β-hydroxy-D-homopregna-1,4,8-triene-3,20-dione.

7. The compound according to claim 2 which is 17a,21-bis(butyryloxy)-11β-hydroxy-D-homopregna-1,4,8-triene-3,20-dione.

8. The compound according to claim 2 which is 17a,21-bis(butyryloxy)-6α-fluoro-11β-hydroxy-D-homopregna-1,4,8-triene-3,20-dione.

9. The compound according to claim 2 which is 21-acetoxy-6α-fluoro-11β,17a-dihydroxy-D-homopregna-1,4,8-triene-3,20-dione.

10. The compound according to claim 2 which is 21-acetoxy-17a-hydroxy-D-homopregna-1,4,8-triene-3,11,20-trione.

11. The compound according to claim 2 which is 11β,17a,21-trihydroxy-D-homopregna-1,4,8-triene-3,20-dione.

12. The compound according to claim 2 which 6α-fluoro-11β,17a,21-trihydroxy-D-homppregna-1,4,8-triene-3,20-dione.

13. The compound according to claim 2 which is 17a,21-dihydroxy-D-homopregna-1,4,8-triene-3,11,20-trione.

14. The compound according to claim 2 which is 11β,17a,21-trihydroxy 6α-methyl-D-homopregna-1,4,8-triene-3,20-dione.

15. The compound according to claim 2 which is $\Delta^8$-D-homoprednisone -21-phosphate.

16. The compound according to claim 2 which is $\Delta^8$-D-homoprednisolone-21-hemisuccinate.

17. The compound according to claim 2 which is $\Delta^8$-6α-fluoro-D-homoprednisolone-21-hemisuccinate.

18. The compound according to claim 2 which is $\Delta^8$-6α-methyl-D-homoprednisolone-21-hemisuccinate.

19. The compound according to claim 2 which is 21-acetoxy-11β,17a-dihydroxy-D-homopregna-1,4,8-diene-3,20-dione.

20. The compound according to claim 2 which is 17a-butyryloxy-21-chloro-11β-hydroxy-D-homopregna-1,4,8-triene-3,20-dione.

* * * * *